(12) United States Patent
Reynolds et al.

(10) Patent No.: US 10,406,512 B2
(45) Date of Patent: Sep. 10, 2019

(54) METAL-ORGANIC FRAMEWORK FUNCTIONALIZED POLYMERIC COMPOSITIONS

(71) Applicant: Colorado State University Research Foundation, Fort Collins, CO (US)

(72) Inventors: Melissa M Reynolds, Fort Collins, CO (US); Jacqueline L Harding, Golden, CO (US); Megan J Neufeld, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 17 days.

(21) Appl. No.: 15/303,672

(22) PCT Filed: Apr. 24, 2015

(86) PCT No.: PCT/US2015/027642
§ 371 (c)(1),
(2) Date: Oct. 12, 2016

(87) PCT Pub. No.: WO2015/164821
PCT Pub. Date: Oct. 29, 2015

(65) Prior Publication Data
US 2017/0028390 A1    Feb. 2, 2017

Related U.S. Application Data

(60) Provisional application No. 62/133,571, filed on Mar. 16, 2015, provisional application No. 61/984,436, filed on Apr. 25, 2014.

(51) Int. Cl.
| | | |
|---|---|---|
| *B01J 31/12* | (2006.01) | |
| *B01D 53/02* | (2006.01) | |
| *B01J 20/32* | (2006.01) | |
| *B01J 23/72* | (2006.01) | |
| *B01J 35/06* | (2006.01) | |

(52) U.S. Cl.
CPC ............ *B01J 31/123* (2013.01); *B01D 53/02* (2013.01); *B01J 20/3212* (2013.01); *B01J 20/3219* (2013.01); *B01J 20/3236* (2013.01); *B01J 20/3265* (2013.01); *B01J 23/72* (2013.01); *B01J 35/06* (2013.01)

(58) Field of Classification Search
None
See application file for complete search history.

(56) References Cited

U.S. PATENT DOCUMENTS

2012/0115961 A1    5/2012   Hafizovic et al.
2013/0313193 A1   11/2013   Nair et al.

FOREIGN PATENT DOCUMENTS

| WO | WO2010/148463 | 12/2010 | |
|---|---|---|---|
| WO | WO 2012/00214 A2 * | 2/2012 | ............ A01N 25/10 |
| WO | WO2012/077030 | 7/2012 | |
| WO | WO2013/059527 | 4/2013 | |

OTHER PUBLICATIONS

International Search Report and Written Opinion of the International Searching Authority in PCT/US2015/027642, dated Jul. 8, 2015, 13 pages.
International Search Report and Written Opinion of the International Searching Authority in PCT/US2015/027643, dated Oct. 29, 2015, 13 pages.
Shekhah et al.: "Step-by-Step Route for the Synthesis of Metal-Organic Frameworks.", Journal of the American Chemical Society, vol. 129, No. 49., 2007, 2 pages.
Silva Pinto et al.: "In situ synthesis of a Cu-BTC metal-organic framework (MOF 199) onto cellulosic fibrous substrates: cotton.", Cellulose., vol. 19, No. 5, 2012, 9 pages.

* cited by examiner

*Primary Examiner* — Yun Qian
(74) *Attorney, Agent, or Firm* — Faegre Baker Daniels LLP

(57) ABSTRACT

A polymeric composition includes an organic polymeric substrate and metal-organic frameworks on the surface of the polymeric substrate. The metal-organic frameworks cover at least 90% of the surface area of the polymeric substrate.

12 Claims, 10 Drawing Sheets

METAL-ORGANIC FRAMEWORK FUNCTIONALIZED POLYMERIC COMPOSITIONS

CROSS-REFERENCE TO RELATED APPLICATION

This application is a national stage application of PCT Application No. PCT/US2015/027642, internationally filed Apr. 24, 2015, which claims priority to Provisional Application No. 61/984,436, filed Apr. 25, 2014 and Provisional Application No. 62/133,571, filed Mar. 16, 2015, which are herein incorporated by reference in their entirety.

TECHNICAL FIELD

The current invention relates to metal-organic frameworks and more specifically to polymeric materials including metal-organic frameworks and methods of forming such materials.

BACKGROUND

Metal organic frameworks (MOFs) are a class of materials whose synthetic versatility and porous crystalline frameworks have propagated their exploration across the spectrum of materials chemistry including gas storage, chromatography, catalysis, and, most recently, biomedicine. However, realistic applications of MOFs have been inhibited primarily due to a lack of thermal stability as well as the uncontrollable release of incorporated payloads, such as hydrogen for fuel cells and therapeutic molecules when used as drug delivery vehicles.

In biological applications, site localized effects are critical towards the ultimate success of materials. Thus, the dispersion of fine powders consisting of MOFs are typically undesirable. As such, the integration of MOFs with solid supports can lead to the potential use of MOFs in previously unrecognized applications. Composite MOF materials, also known as mixed matrix membranes, may be prepared by dispersing MOF particles, such as CuBTC, into polymeric matrices and may facilitate the use towards gas separations and catalysis. The incorporation of these inorganic frameworks into materials creates a symbiotic system allowing enhanced properties of both systems involved. However, these systems have several shortcomings, including leaching.

One method for preparation of composite MOF materials include the growth of MOFs onto thin films of the surfaces of self-assembled monolayers (SAMs) using gold substrates. The widespread use of gold substrates in materials applications is not feasible from a material or economic standpoint. Rather the use of functionalized polymeric materials that can be prepared in large batches and/or tuned for specific applications would provide more suitable growth platforms for MOFs. A second technique involves a layer by layer growth method by exposing the SAMs to metal ions and the ligand precursor separately, creating a "bottom-up" technique allowing the formation of flat layers of surface MOFs (SURMOFs). Recently this idea has been applied to polymer materials, for example, CuBTC was grown onto polyacrylamide through a layer by layer growth method. SURMOFs open the realm for materials of diverse applications, all kinds of structures including silica, nanoparticles. However, the functionalization of the polyacrylamide was not sufficient.

The functional use of MOFs in biomedicine requires the incorporation of the MOF directly onto a biocompatible support. Ideally, solid supports would be composed of existing materials used in the preparation of current medical devices or by using natural polymers. Natural polymers including dextran and chitosan have been rigorously investigated for their potential use in biomedical devices. However, they often fall short as a result of structural deficiencies required for biomedical devices. Cellulose is another natural polymer, which in the form of cotton provides a robust material which is naturally biocompatible, abundant, and easily functionalized.

The preparation of therapeutic textiles utilizing cellulose as the polymeric substrate has historically been geared towards the development of antimicrobial materials. To date silver is the predominant metal ion used as an antimicrobial agent, but more recently copper has generated increasing interest. Towards this end, the fabrication of textiles with incorporated Cu-nanoparticles for use as antimicrobial textiles is reported. The direct growth of CuBTC onto natural fibers including cellulose and silk has been previously explored and demonstrated promising attributes towards antimicrobial activity. However, previously described methods provided low functionalization. Further, the therapeutic action of the materials was restricted solely to the decomposition of the frameworks resulting in the release of $Cu^{2+}$ ions to drive the antimicrobial action. Rather than solely emphasizing the potential of MOF-textiles as antimicrobial agents as a result of their destruction, we propose capitalizing on the potential for MOFs in generating therapeutics that can not only induce antimicrobial activity but also play a role in the promotion of wound healing by maintaining the stability of the MOF on the surface and produce a biological molecule. Use of these materials as bandages or protective gauze at the site of an open wound could enhance wound healing and allow for therapeutic activity as the material degrades, creating an ideal biomedical material. The surface modified polymeric substrates can be used with other devices such as cardiovascular devices (catheters, heart valves, shunts, vascular grafts, patches, etc.).

MOF materials that can bridge the gap between heterogeneous catalysis and drug delivery can revolutionize the development of biomedical devices. Traditionally the use of MOFs as drug delivery vehicles relied on the subsequent incorporation of therapeutics into the pore space. While this has been explored as a viable method for delivery therapeutics it remains limited by the often uncontrollable release of therapeutics, the restriction that only one mode of therapeutic action can be achieved, and that the supply of therapeutics is restricted to the amount that can be incorporated into the MOF. Rather than relying on synthetic therapeutics, nitric oxide is a naturally occurring molecule responsible for governing roles in the immune system and in restoring healthy function to cells and tissues. The exploration of MOFs as heterogeneous catalysts for the generation of nitric oxide (NO) is particularly interesting due to the use of bioavailable substrates, S-nitrosothiols (RSNOs), as an endogenous source of NO. Through the use of RSNOs a theoretically infinite supply of NO is provided by the host environment and the rate at which NO is generated is governed by the particular RSNO substrate.

SUMMARY

A polymeric composition includes an organic polymeric substrate and metal-organic frameworks on the surface of the polymeric substrate. The metal-organic frameworks cover at least 90% of the surface area of the organic polymeric substrate.

A method of forming a polymeric composition includes carboxymethylation of an organic polymeric substrate and growth of metal-organic frameworks on the surface of the organic polymeric substrate by exposing the substrate to a metal ion containing solution followed by exposing the substrate to a ligand containing solution.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
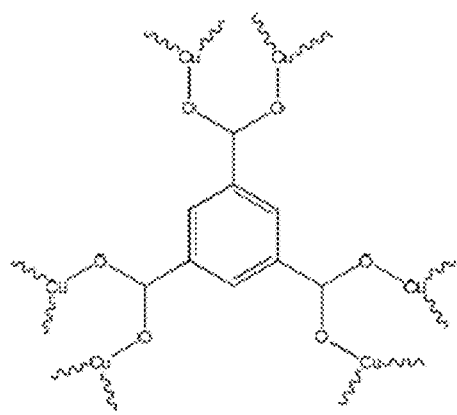
FIG. 1 is a diagram of an exemplarily paddlewheel motif.

This disclosure describes biocompatible compounds, compositions, methods, and uses that may be suitable for use on or with medical devices for use with vertebrate animals or in industrial applications where antimicrobial action is needed. Polymeric compositions described herein that have the ability to produce nitric oxide (NO) from mono or multilayers of crystalline structures, such as MOFs at the surface. In some embodiments, a composition includes the metal-organic frameworks with other secondary therapeutic agents. The metal-organic framework can be further coated with a second polymeric layer or left uncoated.

Also described herein is a new method for growing metal-organic frameworks as crystalline structure on the surface of organic polymeric substrates. Previously, metal-organic frameworks were grown by the deposition of metal-organic frameworks onto surfaces using a liquid phase layer by layer approach that is often time consuming with low yields. The approach described herein uses a layer by layer method which decreases the time required to deposit metal-organic frameworks onto a functionalize surface of the organic polymeric substrate. In addition, the method described herein can provide for catalytic sites at the surface of the organic polymeric substrates that can be used to produce the biological molecule nitric oxide (NO).

As described herein, polymeric substrates with a MOF grown from the surface thereof may be capable of overcoming biofouling or treating diseases, such as clinically relevant diseases or complications. For example, the composition described herein may be used in conjunction with treating cardiovascular diseases, wound healing/closure and/or infection. In some embodiments, the composition described herein may be fabricated into a device, such as a biomedical device, through an extrusion process without a loss of structural integrity or diminished activity towards NO generation. In some embodiments, the composition described herein may also be in the form of disposable papers towels, linens, etc. that are antimicrobial. In further embodiments, the compositions described herein may be used as coatings and material compositions for fabricating medical devices.

For convenience, before further description of the present invention, certain terms used in the specification and examples are described here. These definitions should be read in light of the remainder of the disclosure and understood as by a person of skill in the art. Also, the terms "including" (and variants thereof), "such as", "e.g.", "i.e." as used herein are non-limiting and are for illustrative purposes only.

The articles "a" and "an" are used herein to refer to one or to more than one (i.e. to at least one) of the grammatical object of the article. By way of example, "an element" means one element or more than one element.

"Metal organic framework" consists of linkers coordinated to metals resulting in a 1-dimensional, 2-dimensional, or 3-dimensional structure with well-defined and repeated structural characteristics throughout the material.

"Linker" is a multidentate ligand that binds to metals through coordinate covalent bonds such that it acts as a connector between geometric centers.

"Secondary building unit" is a metal or multiple metals coordinated to organic linkers or other ligand molecules that act as a geometric center for a metal-organic structure.

"Host-guest" is a term that describes the relationship between a discrete compound ("guest") that is located within the pores or open spaces of a metal-organic compound ("host"). In some embodiments, the discrete guest and the metal-organic compound in this relationship are not strongly covalently bonded. For example, the discrete guest compound, such as carbon dioxide gas, is stored in the pores and open spaces of the host, such as MOF compounds.

"Porosity" describes the size of the void spaces in a material. The higher the void space compared to material space, the higher the porosity. Porosity can range from 0-100%.

"Catalysis" refers to the process in which the rate of a chemical reaction is increased by adding an additional chemical compound. In the process, the added chemical compound is not consumed by the reaction. The process usually occurs, but is not limited to, by lowering the activation energy required to promote the forward rate of the reaction. It may also promote increased rates by preorganization or physical arrangement of the reaction components making increased reaction rates more probable.

As used herein, "secondary therapeutic agent" refers to compounds that cause a desirable and beneficial physiological result in response to the compound. Exemplary compounds are described herein.

"Polymer" is a molecule composed of repeating structural or constitutional units, usually referred to as monomers, connected by covalent chemical bonds. Polymers can consist of the same or differing repeat units in order or random fashion. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth. As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating), and block copolymers. Polymers can include both naturally occurring and synthetic materials.

"Producing" is a generic term used to describe all mechanisms of delivery including generating and releasing modes.

"Biocompatibility" is a generic term that describes an interaction or relationship with physiological or biological systems.

"Medical device" refers to product which is used for medical purposes in patients, in diagnosis, therapy, treatment, or surgery. If applied to the body, the effect of the medical device can be physical or chemical.

"Aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, —$OCF_3$, —$NO_2$, —CN, —NC, —OH, alkoxy, amino, —$CO_2H$, —CO~alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

"Heteroaryl" refers to a monocyclic or polycyclic ring system, preferably a monocyclic or bicyclic ring system, containing one or more aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —$OCF_3$, —$NO_2$, —CN, —NC, —OH, alkoxy, amino, —$CO_2H$. —$CO_2$~alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As described herein, in some embodiments, a polymeric composition includes a polymeric substrate functionalized with biomimetic crystalline structures, such as metal-organic frameworks. For example, the polymeric composition may include a polymeric substrate containing metal-organic frameworks on at least a portion of a surface of the polymeric substrate. Optionally, the polymeric composition may also include one or more secondary therapeutic agents.

In some embodiments, the metal-organic frameworks may attach or bind to the surface of the polymeric substrate for example at anchor points. As described herein, in some embodiments, carboxymethylation of the substrate may be performed followed by one or more deposition processes to produce layer growth of the metal-organic frameworks. In embodiments containing one or more therapeutic agents, the therapeutic agents may be incorporated into the MOF and/or into the polymeric substrate.

The polymeric composition described herein has an increased functionalization as compared to previously described compositions. For example, in some embodiments, the metal-organic frameworks may cover greater than 10, 15 or 20% of the surface of the polymeric substrate. In some embodiments, the metal-organic frameworks may cover all or substantially all the surface area of the polymeric substrate. For example, in some embodiments, the metal-organic frameworks may cover 90% or greater of the surface area of the polymeric substrate, and in some embodiments, may cover from about 90-98% of the surface area of the polymeric substrate. As used herein, surface area refers to the surface area of the polymeric substrate exposed to the metal-organic framework and does not include portions of the polymeric substrate which may be masked or which may otherwise prohibit the formation of the metal-organic frameworks.

The polymeric composition may be used in biomedical or industrial applications. In some embodiments, the polymeric composition may be incorporated into a whole device, such as a medical device for external or internal applications, or a portion of a device. For example, the polymeric composition may be incorporated into external applications such as bandages in wound healing applications. The polymeric composition may also be incorporated into hernia patches, sutures and stitches. In some embodiments, the polymeric composition has mechanical properties that match the application. For example, when the polymeric composition is incorporated into a bandage application, the polymeric composition or the bandage device it is incorporated into remains sufficiently strong until the surrounding tissue has healed and/or does not invoke an inflammatory or toxic response. For biodegradable applications, the polymeric composition may be metabolized in the body after fulfilling its purpose, leaving no trace. Further, the polymeric composition may be easily processed into the final product form, may demonstrate acceptable shelf life, and may be capable of sterilization by acceptable methods such as ethylene oxide, gamma, or auto-clave.

In some embodiments, the polymeric composition may be incorporated into a biomaterial or biomedical device without incurring structural damage. For example, in some embodiments, the metal-organic frameworks may be incorporated into the polymeric substrates to form a polymeric composition which may then be fabricated into a biomedical device, such as through an extrusion process, without loss of structure integrity or diminished activity towards NO generation.

The polymeric substrate may include one or more suitable polymers, including materials comprised of cellulose, silk, fibrous synthetic polymers, and/or biomedical grade polymers. Example synthetic polymers include but are not limited to polyurethane (PU), polyesters, polyethers, silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly(vinylidene chloride), or fluorinated polymers such as polytetrafluoroethylene (PTFE). These synthetic materials can be used as homopolymers or multi-component polymers (i.e., copolymer, tri-polymers, etc.). The polymers may be hydrophobic or hydrophilic or contain regions of both hydrophobicity and hydrophilicity.

The polymeric substrate may also include one or more naturally occurring polymers such a fibers, silks, cellulose and sugars. In some embodiments, the polymeric substrate may contain at least one synthetic polymer and at least one naturally occurring polymer.

The polymeric substrate may be an organic polymeric substrate. For example, the polymeric substrate may be fibers, silks, cellulose, sugars and combinations thereof.

In some embodiments, the polymeric substrate may be soft substrate. For example, in some embodiments, the polymeric substrate may have a Shore A hardness of less than 90, such as a Shore A hardness of from 0 to 90. For example, in some embodiments, the polymeric substrate is cellulose and more specifically is cotton.

The metal-organic frameworks bound to the surface of the polymeric substrate. The metal organic frameworks (MOFs) include a metal and linker.

The metal-organic compounds have linkers that are polydentate and bind to at least two or more metals. For example, terephthalic acid and 1,3,5-benzenetricarboxylic acid (trimesic acid) are two common metal-organic linkers with multiple metal-binding sites.

Terephthalic acid:

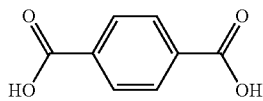

Trimesic acid:

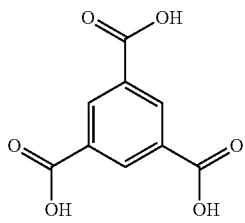 [SMILES: O=C(O)c1cc(C(=O)O)cc(C(=O)O)c1]

Suitable polydentate linkers may have the same or different chemical groups. In various embodiments, the polydentate organic linkers may have a formula I, II, III, IV, or V:

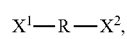   I

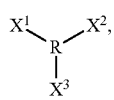   II

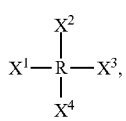   III

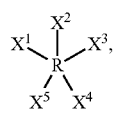   IV

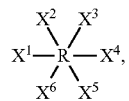   V wherein $X^1$, $X^2$, $X^4$, $X^5$ and $X^6$ are each independently selected from the group consisting of H, $NH_2$, $CO_2H$, SH, nitrogen-containing heteroaromatic compounds, and nitrogen-containing heterocycles, $X^3$ is selected from the group consisting of H, $NH_2$, $CO_2H$, SH, nitrogen-containing heteroaromatic compounds, and nitrogen-containing heterocycles, C(=O)NHR', C(=O)OR', C(=O)SR', N(H)C(=O)R', OC(=O)R', and SC(=O)R';

R is selected from the group consisting of aromatic compounds, heteroaromatic compounds, cycloalkanes, and heterocycles; and R' is a therapeutic agent having one of more functional groups consisting of $NH_2$, $CO_2H$, SH, C(=O)$NH_2$, C(=O)OH and C(=O)SH.

In some embodiments, the nitrogen containing heteroaromatic compound is selected from a group consisting of the following: pyrroly (e.g., pyrrol-2-yl, pyrrol-2-yl), imidazolyl (i.e., imadazol-2-yl, imidazole-4-yl, imdazol-5-yl), pyrazolyl (e.g., pyrazol-3-yl, pyrazol-4-yl, pyrazol-5-yl), oxazolyl (e.g., oxazol-2-yl, oxazol-4-yl, oxazol-5-yl), isoxazolyl (e.g., isoxazol-3-yl, isoxazol-4-yl, isoxazol-5-yl), thiazolyl (e.g. thiazol-2-yl, thiazol-4-yl, thiazol-5-yl), isothiazolyl, (e.g., isothiazol-3-yl, isothiazol-4-yl, isothiazol-5-yl,), triazolyl (e.g., 1, 2, 3-triazol-4-yl, 1, 2, 3-triazol-5-yl, 1, 2, 4-triazol-3-yl, 1, 2, 4-triazol-5-yl), oxadiazolyl (e.g., 1,2,5-oxxadiazol-3-yl, 1, 2, 5-oxadiazol-4-yl), tetrazolyl (e.g., tetrazol-5-yl), pyridinyl (e.g pyridine-2-yl, pyridine-3-yl, pyridine-4-yl), pyrazinyl (e.g., pyrazin-2-yl), pyrimidinyl (e.g., pyrimidin-2-yl, pyrimidin-3-yl, pyrimidin-4-yl), pyridazinyl (e.g., pyridazin-3-yl, pyridazin-4-yl), triazinyl (e.g., 1, 2, 3-triazin-4-yl, 1, 2, 3,-trizin-5-yl, 1, 2, 4,trizin-3-yl, 1, 2, 4,-trizin-5-yl, 1, 2, 4,-trizin-6-yl), and tetrazynyl (e.g., 1,2,3,4-tetrazin-5-yl, 1,2,4,5-tetrazin-3-yl).

In some embodiments, the nitrogen-containing hetrocyclie is selected from the group consisting of pyrrolidinyl, imidazolidinyl, pyrazolidinyl, oxazolidinyl, oxazolinyl, theazolidinyl, dithiazolyl, peperidinyl, piperazinyl, morpholinyl and thiazinyl.

In some embodiments, R is selected from the group consisting of cyclopentane, cylcohexane, cycloheptaine, cyclooctane, and adamantine. In some embodiments, R is selected from the group consisting of benzene, naphthalene, phenanthrene, 1,5a'-dihydropyrene, 1,1'-biphenyl, 1, 1':4', 1"-terphenyl, 5'-phenyl-1, 1': 3', 1"-terphenyl, catechol, pyrazine, pyridine, 2,2'-biyridine, 3,3'bipyridine, 4,4'-bipyridine, and 1,3,5-tri(Pyridin-4-yl)benzene.

In some embodiments, the polydentate organic linker has a formula VI, VII, or VIII:

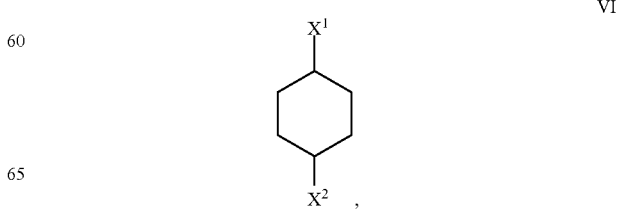   VI

IX, X, XI or XII:

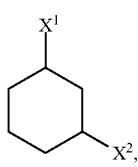
VII

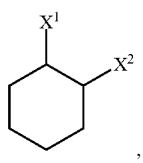
VIII

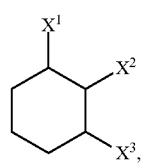
IX

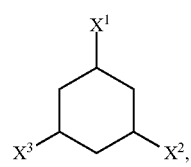
X

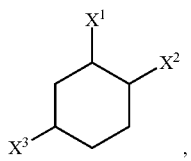
XI

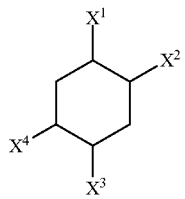
XII

Wherein $X^1$, $X^2$, $X^3$ and $X^4$ are defined herein.

In some embodiments, the polydentate organic linker has the formula XIII or XIV:

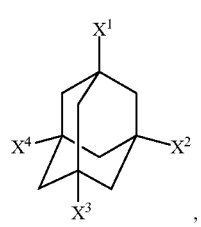
XIII

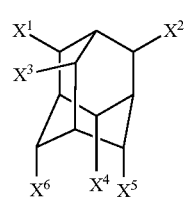
XIV

Wherein $X^1$, $X^2$, $X^3$, $X^4$, $X^5$ and $X^6$ are defined herein.

In some embodiments, the polydentate organic linker has a formula XV:

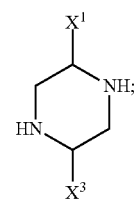
XV

Wherein $X^1$ and $X^3$ are defined herein.

In some embodiments, the polydentate organic linker has a formula XVI, XVII or XVIII:

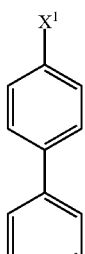
XVI

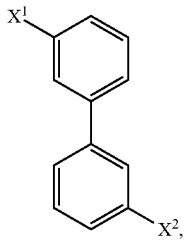
XVII

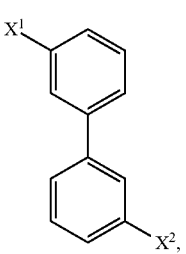
XVIII

XVIII, XIX, XX or XXI:

In some embodiments, the polydentate organic linker has a formula XIX, XX or XXI

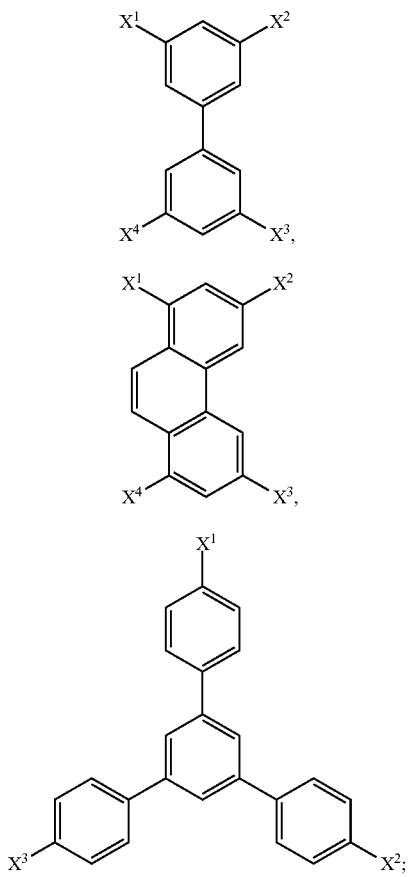

In some embodiments, the polydentate organic linker has a formula XXII or XXIII:

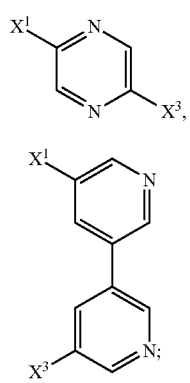

In various embodiments, the polydentate organic linker has a formula XXIV: $R^a$—$X^7$ wherein $X^7$ is selected from the group consisting H, $NH_2$, $CO_2H$, SH, C(=O)$NH_2$, C(=O)OH and C(=O)SH as well as nitrogen-containing heteroaromatic compounds, nitrogen-containing heterocycles, amides, esters, ethers or carbonyl-sulfur compounds. In some embodiments, $X^7$ can be H and $R^a$ can contain at least two heteroatoms.

In other embodiments, the polydentate organic linkers have a formula XXV:

wherein $X^7$ is defined herein.

In some embodiments, the polydentate organic linker is selected from the group consisting of pyrazine, pyridine, 2,2'bipyridine, 3,3'bipyridine, 4/4'-bipyridine, and 1,3,5-tri(pyridine-4-yl)benzene.

The metal-organic compounds contain metals, such as biologically significant metals including, but not limited to, copper, zinc, iron, cobalt, manganese, vanadium, molybdenum, tungsten, chromium, nickel, and aluminum.

In some embodiments, the metal-organic compounds contain metals that maintain their oxidation state within the metal-organic compound. In other embodiments, the metal-organic compounds contain metals that change oxidation states within the metal-organic compound. Compounds of the same metal may contain metals with different oxidation states. For example, a combination of Fe(ll) and Fe(lll) could be combined with an organic linker to produce a mixed-valence metal-organic compound.

The metal-organic compounds may contain secondary building units made from one or more metal atoms combined to the organic linkers. For example, a 'paddlewheel' motif, such as shown in FIG. 1, can involve simultaneous binding of the same linker function to two separate metals to form one larger geometric unit.

Figure 2:
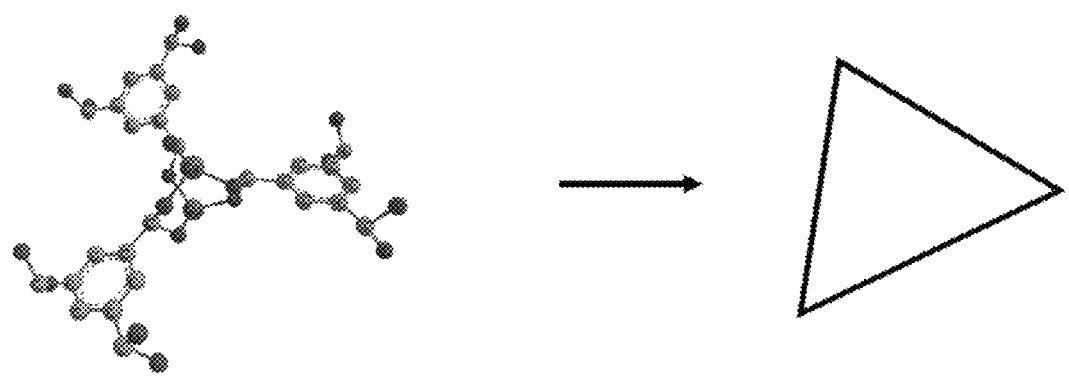
FIG. 2 is a diagram of an exemplarily paddlewheel building unit as a triangular building unit.

The metal-organic compounds may contain secondary building units that act as geometric centers or structural nodes. For example, the paddlewheel building unit can form a triangular building unit as shown in FIG. 2.

In some embodiments, the metal-organic compounds may undergo postsynthetic modification so that they can be functionalized with other chemical moieties after they are formed on the surface.

The metal-organic compounds may have various stereochemistries. For example, in some embodiments, the metal-organic compounds may form symmetric structures, asymmetric structures or may include a combination thereof. That is, the metal-organic compounds may include symmetric structures and asymmetric structures. In some embodiments, the metal-organic compounds may form 1-dimensional, 2-dimensional, and 3-dimensional extended or polyhedral structures that have a range of channel shapes, porosities, sizes, and rigidities.

In some embodiments, the metal-organic compounds may be rigid. In other embodiments, the metal-organic compounds may "breath" to alter open space and pore/channel dimensions.

In some embodiments, the metal-organic compounds can be permeable to gases. For example, in some embodiments, the metal-organic compounds may be selective to gases and other compounds based on structural or chemical properties.

In some embodiments, the metal-organic compounds can be catalytic. For example, Cu-BTC (1,3,5-benzene tricarboxylate) has open metal sites in the metal-organic compound that can act as catalytic centers allowing other reactions to take place at the open coordination sites. In some embodiments the metal-organic compounds may be capable of generating therapeutic amounts of NO under physiological conditions.

In some embodiments, the metal-organic compounds may include functional groups capable of generating NO under physiological conditions. In some embodiments the metal-organic compounds may be capable of generating therapeutic amounts of NO under physiological conditions.

In some embodiments, the metal-organic compounds may be susceptible to degradation. In other embodiments, the metal-organic compounds may not significantly degrade. For example, in some embodiments, the metal-organic compounds may not significantly degrade under physiological conditions, including exposure to physiological fluid or any fluid produced by the body, including but not limited to, subcutaneous fluid, saliva, blood, extracellular fluid, and urine. The susceptibility of a MOF towards degradation may be dictated by the strength of the metal ion coordination networks, and the degradation time of the polymeric composition may be tuned by the selection of the MOF.

In some embodiments, MOF susceptible of degradation may be used for short term applications. For example, in some embodiments it may be desirable to include MOF susceptible of degradation for applications such as bandages and implantable devices meant to degrade. For example, metal-organic frameworks susceptible of degradation may be incorporated into hernia patches and wound closure devices including sutures and stitches.

Additionally or alternatively, in some embodiments, the degradation time of the polymeric composition may be tuned by encapsulating the MOF with a second polymeric material. For example, in some embodiments, a second polymeric material may partially or completely surround, cover or encapsulate the metal-organic frameworks. In some embodiments, the second polymeric material may be deposited following formation of the metal-organic frameworks on the polymeric substrate such that the second polymeric material may also cover the polymeric substrate to the extent it is exposed. Degradation of the second polymeric material may be triggered by a given environmental condition, such as moisture, and the degradation of the second polymeric material will make the MOF accessible. Suitable second polymeric materials include but are not limited to polyvinyl alcohol, collagen, poly(lactic-co-glycolic acid) (PLGA), alginate, chitosan, dextran, polystyrene, nylon, and mixtures and combinations thereof.

In some embodiments, the metal-organic compounds can have host-guest interactions. For example, nitric oxide can have weak intermolecular interactions with the surface of the metal-organic structure.

The polymeric composition may optionally include one or more secondary therapeutic agents. In some embodiments, the secondary therapeutic agents may include or consist of one or more pharmaceutically active compounds that covalently bound to the organic linker in the metal-organic compound. In other embodiments, the secondary therapeutic agents may include or consist of pharmaceutically active compounds that are not specifically found within the open spaces of the metal-organic compound. In still other embodiments, the secondary therapeutic agents may include or consist of pharmaceutically active compounds that are contained with the polymeric substrate and are not associated with the metal-organic compound.

Exemplary suitable non-genetic therapeutic agents include, but are not limited to: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, viricristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-11 receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.). Exemplary genetic therapeutic agents for use in conjunction with the present invention include anti-sense DNA and RNA as well as DNA coding for the various proteins (as well as the proteins themselves): (a) anti-sense RNA, ribozymes, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor a and R, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TKE") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

The polymeric composition may be formed by 1) creation of anchor points or groups on the polymeric substrate; 2) exposure to a metal ion containing solution followed by exposure to a ligand containing solution; and 3) optional additional treatments.

Anchor points or anchor groups on the polymeric substrate provide attachment locations for the metal-organic frameworks. In some embodiments where the MOF is CuBTC, the polymeric substrate may be carboxymethylated. Alternative metal-organic frameworks can be incorporated on the polymeric substrate through modification of the pendent groups on the backbone of the polymer of the polymeric substrate. Derivatization of the pendant groups can be achieved through traditional organic synthetic routs through modification of pendent groups contained on the back bone of the polymeric structure. In some embodiments, pendent groups may include imidazole, triazole and tetrazoles and may facilitate surface growth of metal-organic frameworks constructed from these ligands.

Figure 3:
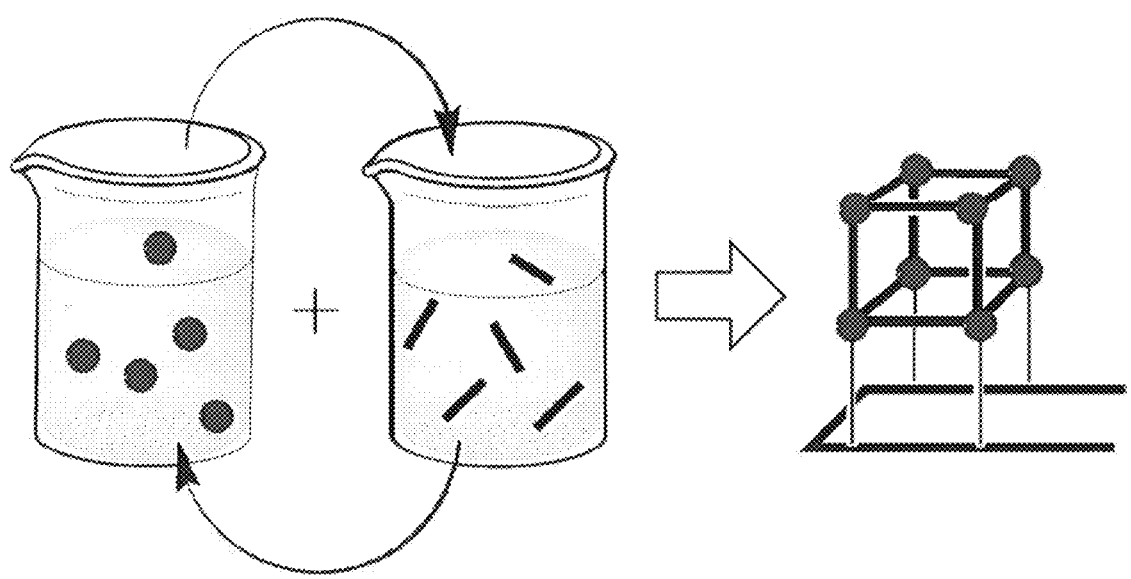
FIG. 3 is a schematic illustration of a process of forming metal-organic compounds on a polymeric substrate.

The metal-organic frameworks may be deposited, such as by ultrasonic deposition, on the functionalized polymeric substrate. For example, the functionalized polymeric substrate with anchor points may be exposed first to a metal ion containing solution followed by exposure to a ligand containing solution. Alternating exposure to the metal ion containing solution and the a ligand containing solution results in layer by layer growth of crystalline MOF structures on the surface of the polymeric substrate as shown schematically in FIG. 3 which illustrates metal ion containing solution, ligand containing solution 20 and polymeric composition 30.

The metal ion containing solution includes metal ions for the formation of the metal-organic frameworks. The polymeric substrate may be exposed to the metal ion containing solution for a sufficient period of time for the metal ions of the solution to interact or be exposed to the polymeric substrate. In some embodiments, the polymeric substrate may be exposed to the metal ion containing solution for less than about 15 minutes or less than about 10 minutes. In some embodiments, the polymeric substrate may be subject to sonication either during or after exposure to the metal ion containing solution.

The ligand containing solution includes ligand precursors for the formation of the metal-organic frameworks. Following exposure to the metal ion containing solution, the polymeric substrate may be exposed to a ligand containing solution for a sufficient period of time for the ligand precursors to interact with the metal ions. In some embodiments, the polymeric substrate may be exposed to the ligand containing solution for less than about 15 minutes or less than about 10 minutes. In some embodiments, the polymeric substrate may be subject to sonication either during or after exposure to the ligand containing solution.

The cycle of exposure to the metal ion containing solution followed by the ligand containing solution may be repeated one or more times. In some embodiments, the cycle may be repeated a sufficient number of times such that entire surface or approximately the entire surface of the polymeric substrate is covered by metal-organic frameworks.

The cycle of exposure to the metal ion containing solution followed by the ligand containing solution may occur at room temperature (e.g., 16-26° C.). Additionally or alternatively, the cycle may occur at atmospheric pressure.

The sonication time and/or speed can impart different structures on the surface. Additional or alternatively, the sonication time and/or speed can affect the surface coverage or degree of functionality of the metal ion and/or ligand on the polymeric substrate. In some embodiments, the sonication time and/or speed may be selected based on the medical device application.

After completion of the one or more cycles, the polymeric substrate may be sonicated to remove any particles or compounds that are not attached or adhered to the polymeric substrate.

The polymeric composition may be subjected to one or more additional processing steps following the formation of the metal-organic frameworks on the surface. For example, a secondary therapeutic agent may be deposited onto the polymeric composition. Additionally or alternatively, a second polymeric material may be added, such as by a deposition process, to the polymeric composition.

Figure 4:
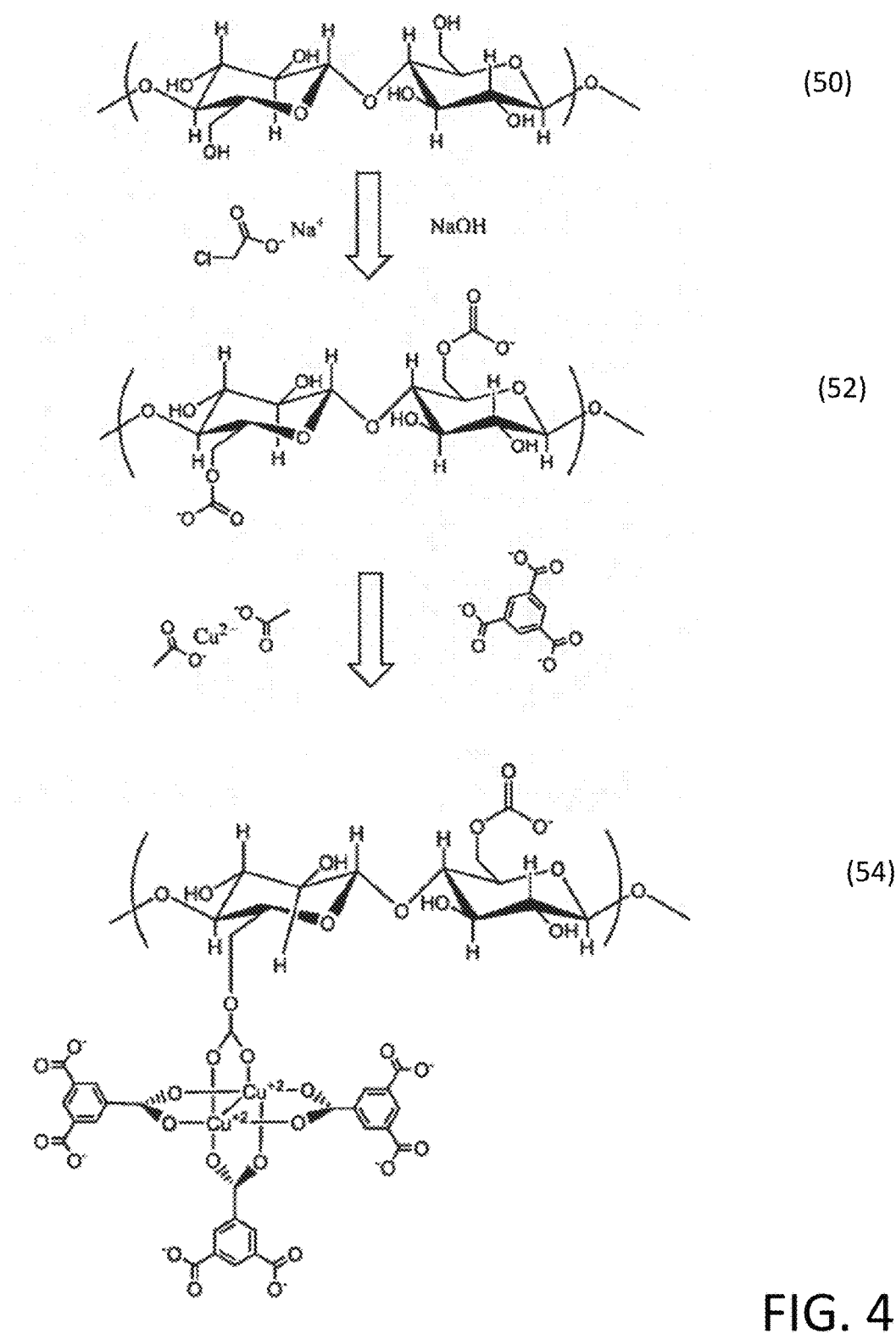
FIG. 4 is a scheme for forming metal-organic compounds on a polymeric substrate.

As described above, in some embodiments, CuBTC may be deposited or attached to the surface of the cellulous substrate. FIG. 4 provides schemes of such a process including providing a cellulous substrate in step 50, carboxylation of the substrate in step 52 and formation of metal-organic frameworks thereon in step 54.

Figure 5:
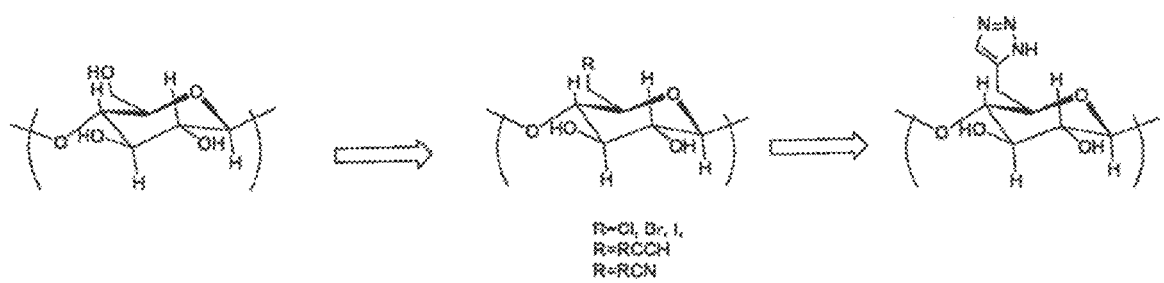
FIG. 5 is another scheme for functionalizing cellulose with a triazole linker.

In another example, CuBTTri may be attached to the surface of the cellulous substrate. Growth of CuBTTri may be achieved in a manner similar to that described with respect to CuBTC except in order to facilitate MOF growth of CuBTTri onto the surface of modified cellulose, the hydroxyl groups must be converted to a different functional group including triazoles, carboxylates, amines, amides, tetrazoles, pyrazoles and pyridines. Some approaches to this conversion include the substitution of the hydroxyl group followed by direct synthesis by using organonitriles, nitriles and ammonia as well as halide substitution followed by with a terminal alkyne group and direct synthesis of the triazole using copper iodide and an azide group such as TMS-azide, sodium azide or azide prepared in situ to form a triazole functionalized cellulose material, creating the linker needed for the initial nucleation of the MOF formation. This would be followed by the addition of the precursor solutions by either a mother solution, layer by layer or by dipping into alternate solutions. Metal precursors could include Cu but also (Co, Fe, Mg, Zn, Al, Ag and other transition metals) or an additional group that is capable of being converted to a triazole using azide chemistry. Functionalization of cellulose with a triazole linker is provided in FIG. 5. In another example, CuBTT may be attached to the surface of the polymeric substrate.

In still further embodiments, the MOF may have water stability. For example, Cu(II)-2,2'-bipyridinebenzene-1,3,5-tricarboxylate (Cu-bipy-BTC) may be grown onto the surface of a biodegradable polymer with hydroxyl groups that can be functionalized, such as cellulose. Growth could be initiated through the same process as previously described for CuBTC growth onto the cellulose substrate due to the presence of the tricarboxylate linkers. Polymeric compositions including metal-organic frameworks having increased water stability would produce polymeric compositions with increased stability in aqueous environments.

The methods described herein can also be used to coat tables, IV poles, and other types of surfaces that are prone to bacteria or viruses.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. Unless otherwise noted, all parts, percentages, and ratios reported in the following examples are on a weight basis.

Example 1

Preparation of CuBTC-Cellulose Hybrid Materials for Bandage Applications

In the following example, cellulose functionalized with carboxymethylated pendant groups served as attachment sites for CuBTC grown in situ using layer by layer growth under sonication, providing ultrafast MOF synthesis. The resulting CuBTC cellulose materials where characterized by XRD, ATR-IR, and SEM. The material was also analyzed for use as a heterogeneous catalyst towards the generation of therapeutic NO.

Functionalizing Cellulose Fabric

Anchoring points in a cellulose (cotton) fabric sample were formed by carboxymethylation using sodium hydroxide as the catalyst. A 1M solution of sodium chloroacetate (1.16 g) and 5% NaOH (2.5 mL) was prepared by dissolving in a total volume of 10 ml. Cellulose material was reacted in the solution for an hour under constant rotation.

Cu-BTC Deposition on Cellulose Fabric

A metal ion containing solution was formed by completely dissolving copper acetate (1.078 g) in 15 mL of millipore water (18 MCI) to obtain a 0.36 mM solution.

A ligand containing solution was formed by dissolving $H_3BTC$ (631 g) in 15 mL of a 1:1:1 ratio DMF:ethanol:water to obtain a 0.2 M solution.

Ultrasonic deposition of Cu-BTC was performed by sequentially dipping the functionalized cotton fabric sample in the copper acetate $(Cu(OAc)_2 \cdot 2H_2O)$ solution, followed by the $H_3BTC$ solution. The cotton sample was dipped in each solution for 5 minutes. A total of 8 alternating cycles were performed, where one alternating cycle consisted of dipping the fabric sample in the metal ion containing solution and then dipping the fabric sample in the ligand containing solution.

After each dipping, the cotton sample was rinsed thoroughly with millipore water to remove any excess reagents. After 8 cycles, the sample was washed for 5 hours in ethanol followed by DMF to remove any Cu-BTC which was not covalently bonded to the cellulose.

Evaluation of NO Release of the CuBTC/cellulous Substrates

NO release experiments were conducted using bioavailable S-nitrosothiols including S-nitrosocysteine (CysNO), S-nitrosocysteamine (CysamNO). The CuBTC/cellulose substrate after in situ growth was added to the NO reaction chamber using ethanol as the solvent to prevent degradation of the catalyst, followed by an excess of the substrate. NO release was monitored in real time by chemiluminescence detection method. Rapid generation of NO was observed in comparison to reactions not containing the catalyst with complete conversion of the substrate to NO in under an hour compared to an excess of 20 hours without a catalyst.

Figure 6:
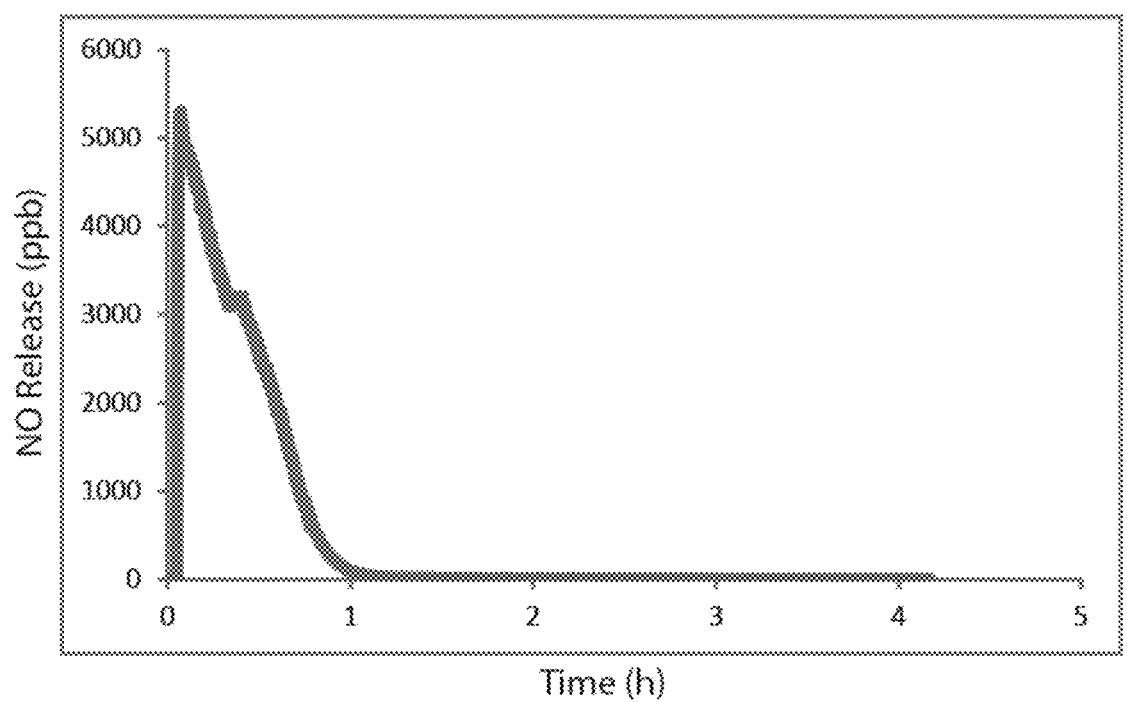
FIG. 6 is a plot of nitric oxide release in parts per billion versus time for a MOF functionalized polymeric substrate.
Figure 7:
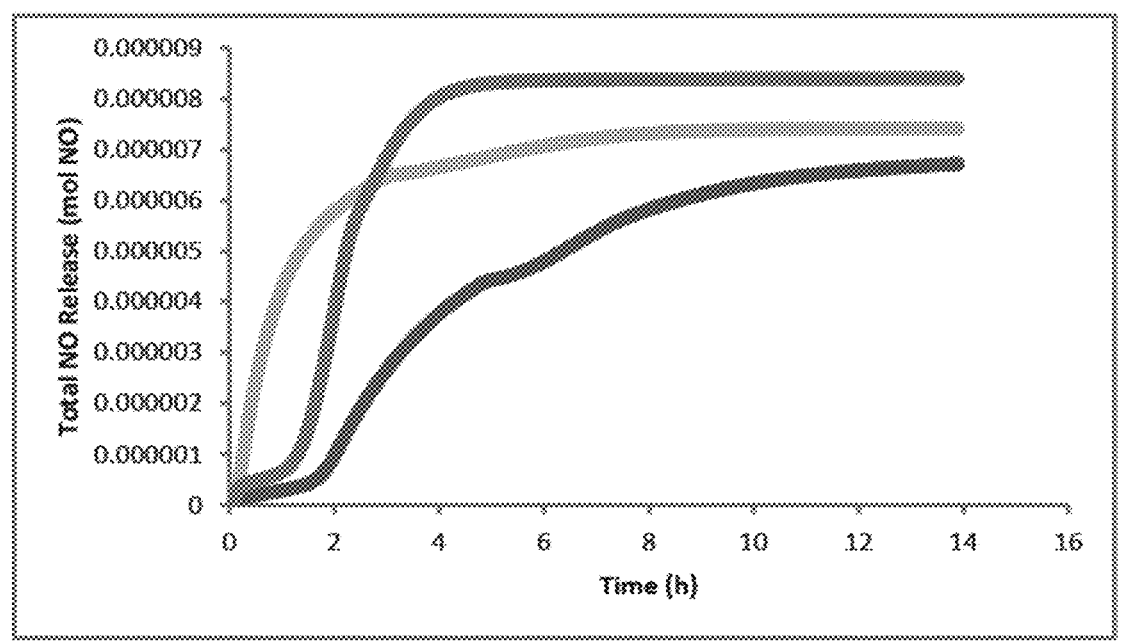
FIG. 7 is a plot of nitric oxide release in mol NO versus time for a MOF functionalized polymeric substrate.

Once the reaction was complete the CuBTC/cellulose substrate was removed from the reaction solution and washed three times with fresh aliquots of ethanol and then investigated for repeat use. Two subsequent reactions of CysNO with the CuBTC/cellulose substrate indicated there was a difference in the reactivity of the substrate with only half of the available substrate converted to NO and the duration of the experiment was prolonged. Compared to the first iteration in which the CuBTC/cellulose substrate catalyzed the generation of 90% of the NO in a 1 hour period, the second iteration resulted in only 50% of the available NO catalyzed from the reaction before halting the reaction in the same one hour period. In the third and final iteration of the experiment the rate of NO generation was significantly reduced with only 35% of the total NO recovered after 1 hour, the reaction was complete after 2 hours with only 50% of the total NO available recovered. The results of the first run are provided in FIG. 6 and the results of all three runs are provided in FIG. 7.

Characterization of the fabric samples were performed via pXRD, SEM, EDX, and IR. All data was processed using Thermo NSS Release candidate 7 software.

Figure 8:
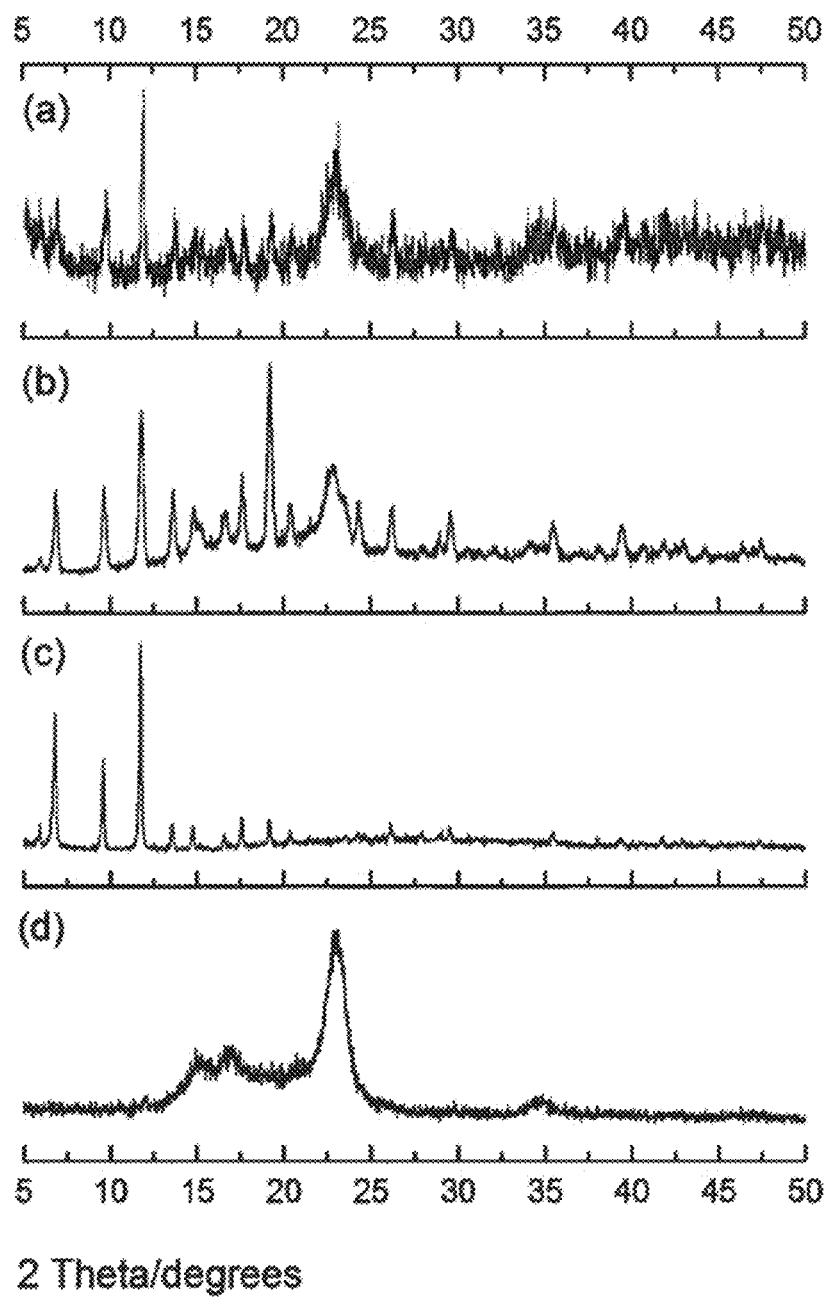
FIG. 8 is powder x-ray diffraction plots for (a) a CuBTC/cellulose substrate after NO release; (b) a CuBTC/cellulose substrate after in situ growth; (c) CuBTC powder; and (d) the initial cellulose substrate.

The cotton samples were evaluated for crystallinity by Powder X-ray diffraction (pXRD) using a Scintag X9 pXRD with CuKa radiation. FIG. 8 is pXRD images of the initial cellulose material (d), the CuBTC powder (c) the CuBTC/cellulose substrates after in situ growth (b), and the CuBTC/cellulose substrates after NO release (a). The broad large peak observed in the cellulose cloth (FIG. 8*d*) arises from the crystalline nature of the polymer. It is observed that the CuBTC/cellulose substrate (FIG. 8*b*) match the reported pattern for CuBTC powder (FIG. 8*c*) with a small increase in intensity due to overlapping of the broad peak observed in cellulose (FIG. 8*d*).

Additionally, comparing the CuBTC/cellulose substrates after NO release (FIG. 8*a*) and the CuBTC/cellulose substrates after in situ growth (FIG. 8*b*), it can be seen that the CuBTC is relatively stable with little change seen before and after the NO release.

Figure 9:
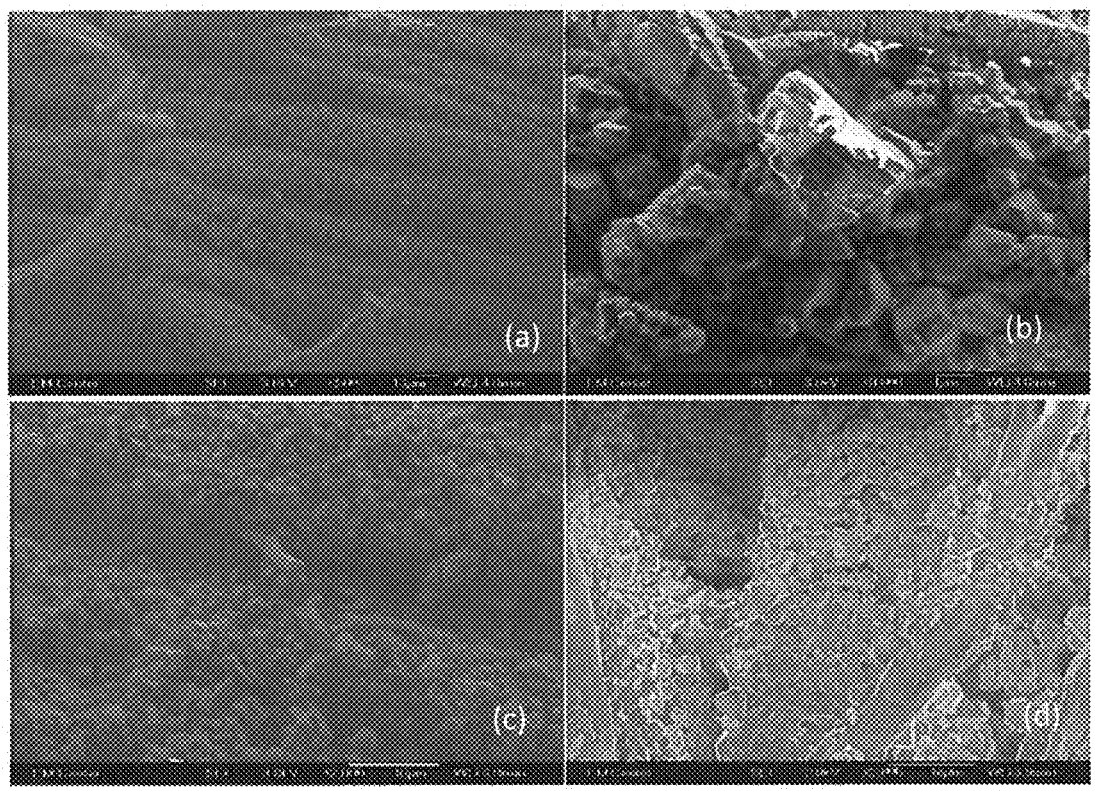
FIG. 9 is SEM images of growth of CuBTC on a cellulose substrate.

Using a JEOL JSM-6500F (FSEM) with an accelerating voltage of 3.0 kV and a working distance of 4.0 mm images were taken at magnification values of 500×, 2,000× and 9,000× and processed for copper distribution using EDX spectroscopy. The EDX spectrum was collected at an accelerating voltage of 5 kV at 130× magnification. FIG. 9 is SEM images of the growth of CuBTC onto the carboxymethylated cellulose substrate at 2000× (a), 9,000× (b), 500× (c) and 2,000× (d) magnification. The SEM images show uniform crystalline formation on surface of the substrate.

Figure 10:
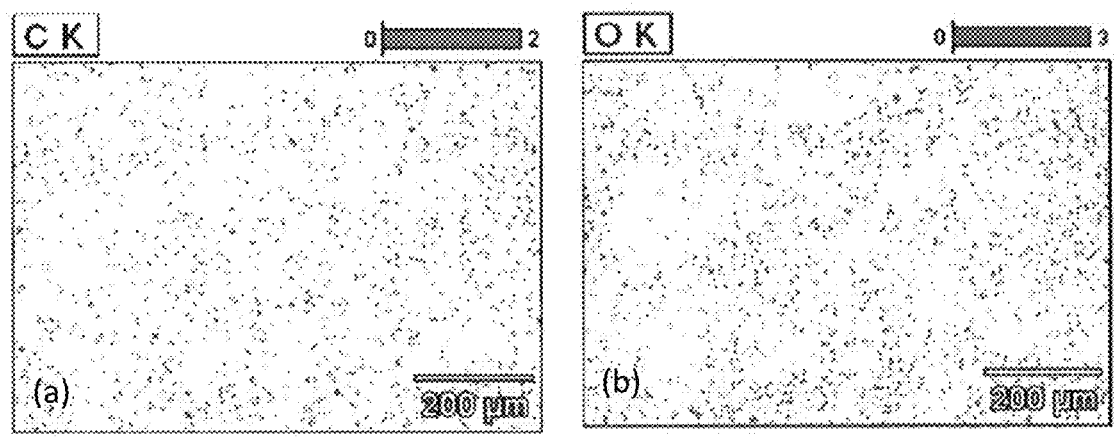
FIG. 10 is EDX mapping of (a) copper and (b) oxygen for a CuBTC/cellulose substrate composition.

EDX mapping of copper and oxygen are provided in FIG. 10, in which (a) is of copper and (b) is of oxygen. The uniform distribution of copper and oxygen suggest uniform distribution of the metal-organic frameworks on the surface of the substrate.

Figure 11:
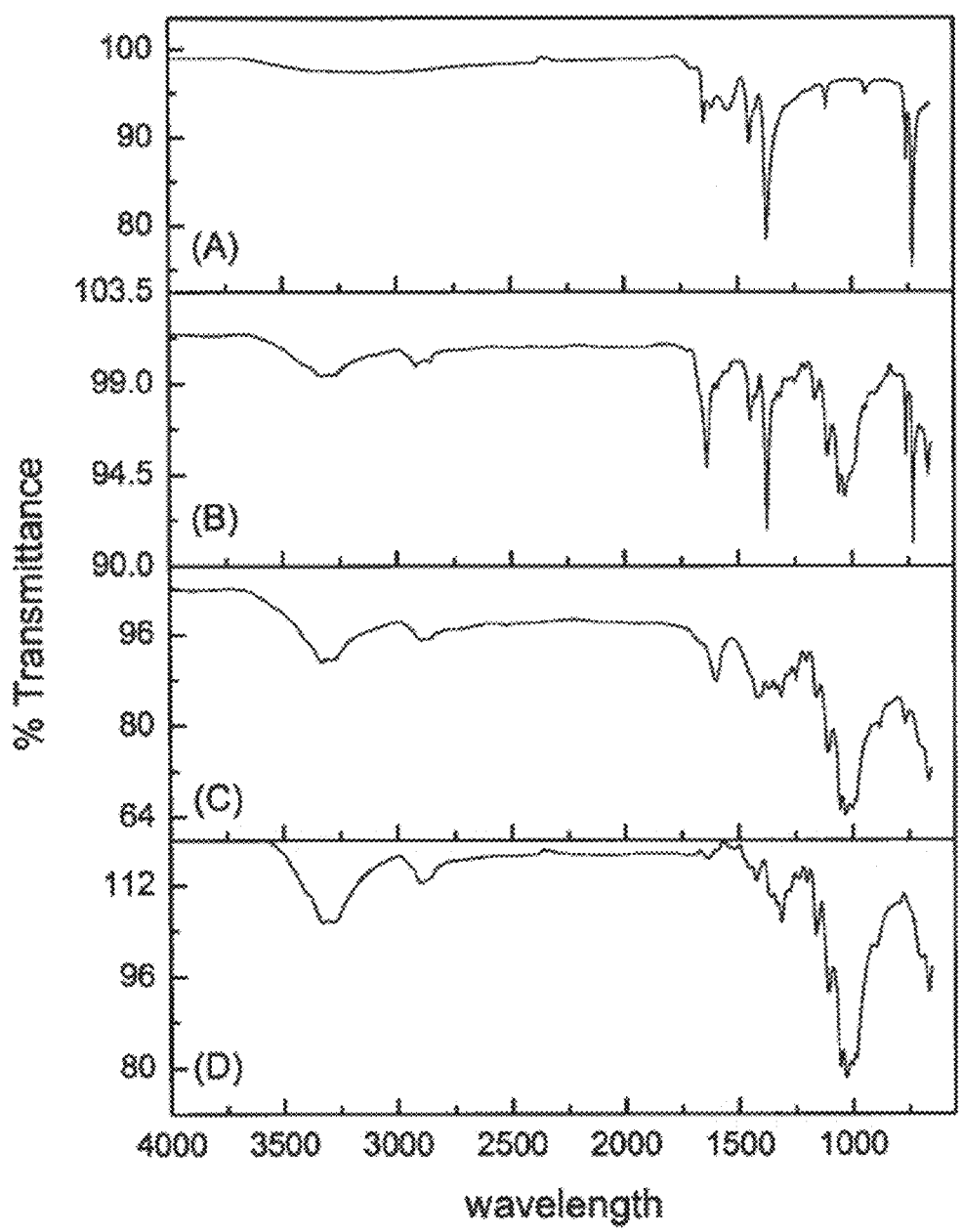
FIG. 11 is ATR-IR spectra of (A) CuBTC powder, (B) CuBTC/cellulose substrate, (C) cellulose substrate after carboxymethylation and (D) cellulose substrate prior to modification.

FTIR was carried out on a Nicolet 6700 spectrometer with a single attenuated total reflectance (ATR) adapter in the range of 400-4000 $cm^{-1}$. ATR-IR spectra are provided in FIG. 11 with (A) of the CuBTC powder, (B) of the CuBTC/cellulose substrates, (C) of the cellulose substrates after carboxymethylation and (D) of the cellulose substrate prior to modification.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features. For example, while the embodiments described above refer to use of the polymeric composition in a medical device or for the treatment of a disease or condition, the polymeric composition may be used in other fields. For example, the polymeric composition may be used in membrane or separations applications.

The following is claimed:

1. A method of forming a polymeric composition having metal-organic frameworks consisting of a metal coordinated with linkers, the method comprising:
    forming a metal ion containing solution containing metal ions for metal of the metal-organic frameworks and is free of ligand precursors for the linkers of the metal-organic frameworks;
    forming a ligand containing solution containing ligand precursors for the linkers of the metal-organic frameworks and that is free of metal ions for the metal of the metal-organic frameworks;
    carboxymethylation of an organic polymeric substrate, the organic polymeric substrate selected from the group consisting of cellulose, fibers, silks, sugars and combinations thereof; and
    layer-by-layer growth of the metal-organic frameworks on the surface of the carboxymethylated organic polymeric substrate by sequentially dipping the substrate in the metal ion containing solution followed by dipping the substrate in the ligand containing solution and repeating the process of sequentially dipping the substrate in the metal ion containing solution followed by dipping the substrate in the ligand containing solution at least once, wherein after each dipping the substrate is rinsed with water to remove excess reagents, and wherein the metal-organic frameworks are selected from the group consisting of CuBTC and $H_3[(Cu_4Cl)_3-(BTTri)_8]$, $H_3BTTri=1,3,5$-tris(1H-1,2,3-triazol-5-yl)benzene) (CuBTTri).

2. The method of claim 1, wherein the growth of the metal-organic frameworks includes repeating the sequential dipping at least two times.

3. The method of claim 1 wherein dipping steps are performed at room temperature.

4. The method of claim 1 wherein the dipping steps are performed at atmospheric pressure.

5. The method of claim 1 wherein the polymeric substrate includes cellulose.

6. The method of claim 5 wherein the polymeric substrate is a fabric.

7. The method of claim 1 and further comprising applying a therapeutic agent to metal-organic frameworks on the polymeric substrate.

8. The method of claim 7 wherein the therapeutic agent is pharmaceutically active compound.

9. The method of claim 1 wherein the metal-organic frameworks do not degrade when exposed to physiological fluid.

10. The method of claim 1 wherein the polymeric substrate has a Shore A hardness value from 0 to 90.

11. The method of claim 1 wherein in the first sequential dipping process, the substrate is dipped in the metal ion containing solution for a time greater than 0 and less than 15 minutes.

12. The method of claim 11 wherein in the first sequential dipping process, the substrate is dipped in the ligand containing solution for a time greater than 0 and less than 15 minutes.

* * * * *